United States Patent [19]

Jaicks

[11] Patent Number: 4,664,104
[45] Date of Patent: May 12, 1987

[54] ANTI-HERPES MODALITY SYSTEM

[76] Inventor: John R. Jaicks, 945 Morris Park Ave., Bronx, N.Y. 10462

[21] Appl. No.: 697,852

[22] Filed: Feb. 4, 1985

[51] Int. Cl.⁴ .......................... A61F 13/00; A61F 5/44
[52] U.S. Cl. ................................. 128/132 R; 604/353
[58] Field of Search ............... 604/328, 329, 349–353; 128/132 R, 760, 761, 762; 285/240; 2/405, 408

[56] References Cited

U.S. PATENT DOCUMENTS

| | | | |
|---|---|---|---|
| 2,371,883 | 3/1945 | Gammeter et al. | 604/349 |
| 2,406,600 | 8/1946 | Forestiere | 128/630 |
| 2,445,694 | 7/1948 | Predmore | 604/351 |
| 2,591,783 | 4/1952 | Craddock | 604/353 |
| 2,873,740 | 2/1955 | Wainwright | 604/349 |
| 3,536,066 | 10/1970 | Ludwig | 128/132 R |
| 4,568,340 | 2/1986 | Giacalone | 604/353 |

FOREIGN PATENT DOCUMENTS

| | | | |
|---|---|---|---|
| 1158507 | 12/1983 | Canada | 604/349 |
| 459968 | 1/1937 | United Kingdom | 2/405 |

*Primary Examiner*—J. L. Kruter
*Attorney, Agent, or Firm*—Lackenbach Siegel Marzullo & Aronson

[57] ABSTRACT

An anti-herpes modality system that includes a garment worn by either the male or female partner of a couple, one of whom has herpes simplex. A sheath member is removably connected to the garment by way of a biasable gripper secured to the open end of the sheath member that is adapted to fit around a toroidal lock secured to the rim of a hole in the genital area of the garment. The toroidal lock may also be biasable. The garment, sheath member, and the seal formed between them are impervious to the passage of herpes virus. Alternatively, a male garment integral with a flexible male sheath members; or a female garment integral with a flexible male sheath member are provided.

5 Claims, 9 Drawing Figures

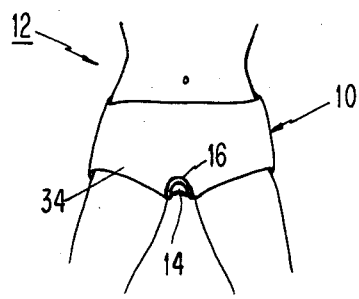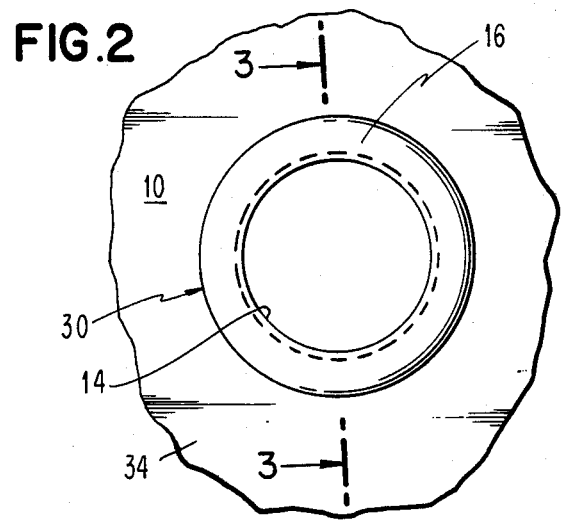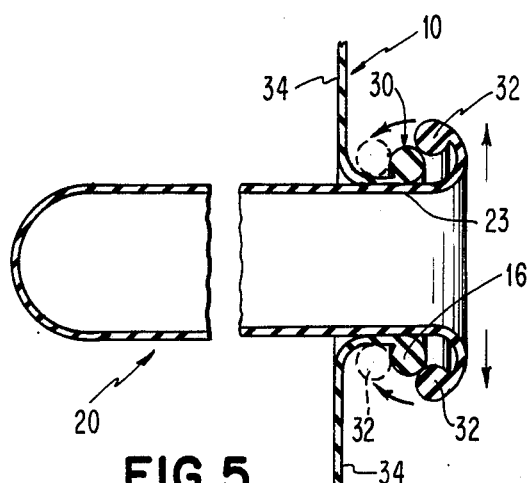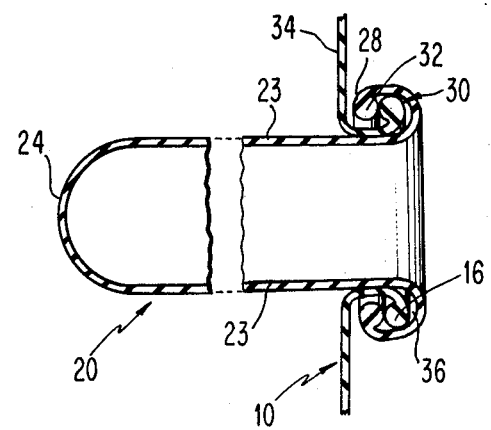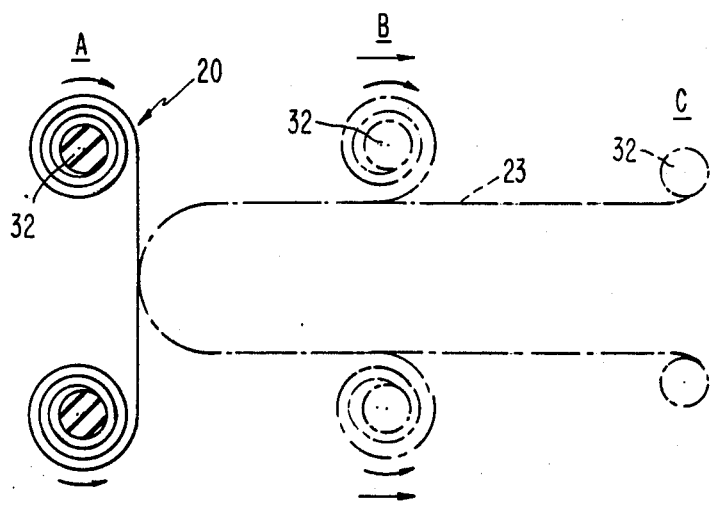

ANTI-HERPES MODALITY SYSTEM

This invention relates generally to the prophylactic devices for the prevention of venereal infection and more particularly to a prophylactic device for the prevention of herpes simplex during coitus.

Herpes simplex is a venereal disease long known in history that attacks humans of both sexes. Humans are the natural hosts of herpes simplex. The Center for Disease Control estimates that about 300,000 new cases of herpes appear each year and that about 25,000,000 persons presently suffer from the disease. Herpes is believed to be spreading among the population in geometric fashion.

Persons affected with herpes are mentally and physically crippled by the disease. Their desire not to transmit the disease to others is diametrically opposed to their natural desire to have sexual relations.

Herpes is transmittable by a person having herpes with an active exascerbation, or lesion. It is also transmittable by a person with herpes who has no active lesion, since it has become known that the person having herpes "sheds" even in the dormant stage of the disease. In addition, there are people who never have a lesion, but who nonetheless act as herpes carriers and shed the disease constantly and who can transmit the disease to others. These carriers can be detected by medical testing.

Once the disease has been confirmed, it is necessary to take steps to contain the disease to the afflicted party and to prevent it from spreading to others.

Unfortunately, presently known prophylactic devices, such as condoms (which are also to prevent conception) to be used during during coitus are not effective in preventing the transmittal of herpes.

SUMMARY OF THE INVENTION

Accordingly, it is a principal object of the present invention to provide an anti-herpes modality system that prevents the transmission of herpes simplex during coitus.

It is another object of the present invention to provide at least one anti-herpes garment and a condom-type device removably connected to the garment so that the transmission of herpes during coitus is prevented.

It is still another object of the present invention to provide an anti-herpes garment to be worn by a male or a female with a condom-type device removably connected to the garment so that the transmission of herpes during coitus is prevented.

It is yet another object of the present invention to provide one anti-herpes garment for a man and one for a woman with a condom-type device that are all interconnected so that the transmission of herpes during coitus is prevented.

In accordance with the above objects, there is provided an anti-herpes modality system for a male partner and a female partner that comprises at least one garment impermeable to the passage of herpes virus worn by one of said partners covering the herpes contagious genital area of the one partner and a sheath member having a generally cylindrical, flexible wall impervious to the passage of herpes virus adapted to fit around the penis of the male partner removably and sealably connected to the garment. The garment forms a circular hole having a rim portion and a toroidal lock secured to the rim. The toroidal lock is preferably biasable. The cylindrical wall of the sheath member has a closed end and a circular open end having a circular edge portion to which is secured a biasable toroidal gripper. The toroidal gripper is adapted to removably engage the toroidal lock. The toroidal lock and the toroidal gripper are for removably connecting the sheath member with the garment and are also for sealing the sheath member with the garment against the passage of herpes virus. The garment is preferably configured as a pair of short pants and is made of soft, flexible material. The garment may be worn by the male or the female partner or one garment may be worn by each.

Alternatively, male and female garments each integrate with a male sheath integral with the garment.

BRIEF DESCRIPTION OF THE DRAWINGS

The invention will now be described with reference to the accompanying drawings, wherein:

FIG. 1 is a frontal view of the anti-herpes garment as worn by a female;

FIG. 2 is a fragmented view of the anti-herpes garment of FIG. 1 showing the connecting area between the garment and the sheath member;

FIG. 3 is a view taken through line 3—3 of FIG. 2;

FIG. 4 is a side sectional view of the sheath member of the modality;

FIG. 5 is a side sectional view of the sheath member being connected to garment component;

DESCRIPTION OF THE PREFERRED EMBODIMENTS

Reference is now made in detail to the drawings wherein particular numerals refer to the same or similar elements throughout the several drawings.

Three embodiments of the invention will be described. With regard to the embodiments, it is to be noted that either the female partner or the male partner will have herpes, or be suspected of having it, with the other partner being free of the disease.

Figure 6:
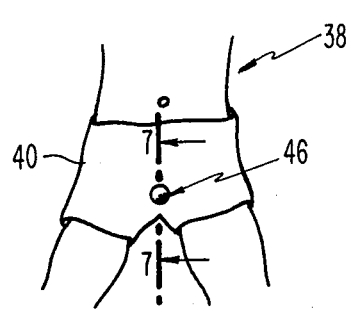
FIG. 6 is a frontal view of the anti-herpes garment as worn by a male.
Figure 7:
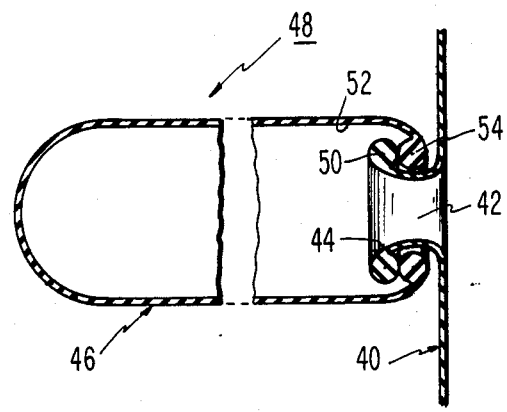
FIG. 7 is a view taken through line 7—7 of FIG. 6.
Figure 8:
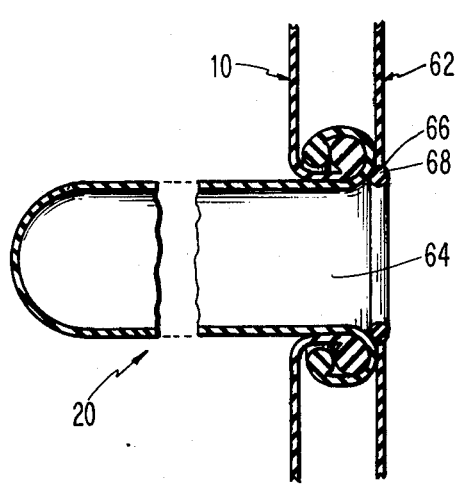
FIG. 8 is a side sectional view of an embodiment of male and female garments being used with the sheath member.

FIGS. 1, 2 and 3 would generally apply to an infected female partner and FIGS. 6 and 7 generally to an infected male partner. FIGS. 7 and 8 are applicable to all cases. It may be said, however, that protection can be given to either non-infected partners in all the embodiments described.

FIG. 1 illustrates an anti-herpes female garment 10 worn by a female partner 12 of a male partner (not shown). Female garment 10 preferably is a typical lower fitted garment such as short pants. Female garment 10 is made of a material that is lightweight, flexible, and impermeable to the passage of herpes virus and excretions. Female garment 10 covers the herpes contagious genital area of female partner 10. Female garment 10 forms a hole 14 at the genital area coextensive with the vagina of female partner 12. Hole 14 is preferably circular and has a circular rim portion 16.

FIG. 2 illustrates in fragmented frontal view the genital area of female garment 10 and a male sheath member 20.

FIG. 3 is a cross-sectional view of female garment 10, and male sheath member 20 showing sheath member 20 operatively positioned through hole 14 of female garment 10.

In the embodiment of FIGS. 1, 2 and 3, an anti-herpes modality system 22 is illustrated and comprises female garment 10 as one component of the system and male sheath member 20 as the other component. Sheath member 20 is adapted to fit over the penis of the male partner. Sheath member 20 is elongated and made of a soft, flexible or pliable material. Sheath member 20 includes an elongated, generally sheath wall 23 made of a flexible material. Sheath wall 23 is generally cylindrical when in the operative mode and encasing the penis. Sheath member 20 is illustrated in FIG. 3 for purposes of exposition operatively extended as if it encloses the penis of the male partner. Sheath wall has a closed end 24 that is extended into and spaced from the entrance of the vagina of the female partner 10 and an opposed circular open end 26 that is positioned at the base of the penis of the male partner. Open end 26 has a circular edge portion 28.

Female garment component 10 and male sheath member component 20 are removably and sealably connected as follows. Rim portion 16 of female garment 10 is secured to a biasable toroidal lock member 30 and edge portion 28 of sheath member 20 is secured to a biasable toroidal gripper member 32. Female garment 10 includes a front wall portion 34 that is disposed around the genital area of female member 10 as shown in FIGS. 2 and 3. Front wall portion 34 and toroidal lock member 30 form a circular cavity 36. Biasable toroidal gripper member 32 is positioned in circular cavity 36, wherein toroidal lock member 30 holds toroidal gripper member 32 in cavity 36. Toroidal lock member 30 also is slightly biased radially inwardly so as to press female garment 10 against the penis of the male partner. Biasable lock member 30 is preferably made of biasable plastic, rubber, or a coiled spring capable of radially biasing against the penis of the male partner. In addition, biasable toroidal gripper member 32 is in a slightly biased mode in cavity 36 so as to form a seal between female garment 10 and sheath member 20 that prevents the passage of the herpes virus from the female partner to the male partner. In particular, toroidal gripper member 32 presses radially inwardly directly against front wall portion 34 and indirectly against sheath member 20. It is to be understood that the presence of the penis causes a resisting force that creates the sealing effect.

FIG. 4 illustrates in cross-section sheath member 20 in a rolled position "A", in a partially unrolled position "B" indicated in phantom lines, and a fully unrolled position "C", also indicated in phantom lines. In position C, sheath wall 23 has been positioned on the penis and toroidal gripper member 32 is ready to be stretched into its biased mode for snap-mounting into circular cavity 36, as shown in FIG. 5. As noted above, once positioned in cavity 36, toroidal gripper member 32 is in a slightly biased mode that causes an inward radial pressure against female garment 12 so as to seal female garment 10 with sheath member 20.

FIGS. 6 and 7 illustrate a male partner 38 of a female partner (not shown) wearing an anti-herpes male garment 40 similar to female garment 10, except that the placement of a hole 42 formed by male garment 40 at the genital area of male partner 38 is situated slightly differently because of the different placement of male and female genital areas. Male garment 40 covers the herpes contagious genital area of male partner 38. Hole 42 is preferably circular and has a circular rim portion 44. A sheath member 46 is operatively positioned as if in the vagina (not shown). Sheath member 46 is removably and sealably connected to male garment 40 to comprise a second embodiment of an anti-herpes modality system 48. Sheath member 46 is similar in construction and design to sheath member 20 of FIGS. 2 and 3. Male garment 40 includes a toroidal lock member 50 disposed around rim portion 44. Toroidal lock member 50 and male garment 40 form a circular cavity 52 that is adapted to receive a biasable toroidal gripper member 54 that is capable of being biased so as to slide over toroidal lock member 50 into cavity 52 where it is slightly biased so as to directly radially press male garment 40 against the penis so as to create an anti-herpes seal between male garment 40 and sheath member 46. Toroidal lock member 50 is preferably biasable radially inwardly so as to grip the penis of the male partner. Biasable toroidal lock member 50 can be made of a biasable plastic, rubber, or a coiled spring biasable radially inwardly. The radial bias of lock member 50 is relatively slight.

A double protection anti-herpes modality system 60 is shown in FIG. 8. System 60 includes female garment 10 and sheath member 20 components described with reference to FIGS. 1, 2 and 3. System 60 further includes a male garment 62 worn by the male partner. Male garment 62 form a circular hole 64 in the genital area of the male partner having a rim 66 to which is secured a biasable toroidal gripper 68 capable of gripping the base of the penis of the male partner.

Figure 9:
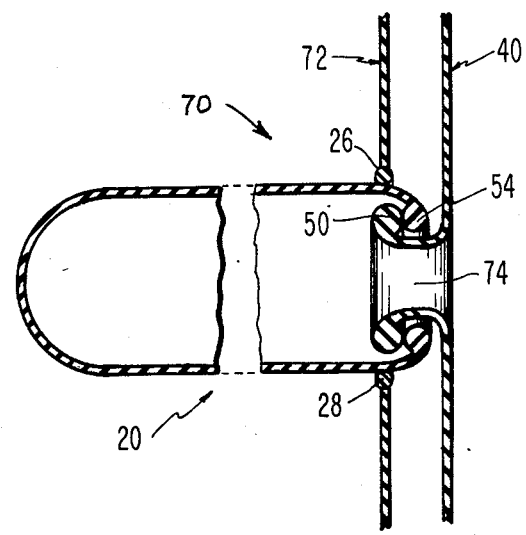
FIG. 9 is a side sectional view of another embodiment of male and female garments being used with the sheath member.

A double protection anti-herpes modality system 70 is shown in FIG. 9. System 70 includes male garment 40 and sheath member 46 components described with reference to FIGS. 6 and 7.

System 70 further includes a female garment 72 worn by the female partner. Female garment forms a circular hole 74 in the genital area of the female partner having a rim 26 to which is secured a biasable toroidal gripper 28 capable of being radially self-biased directly against sheath member 46 and indirectly against toroidal lock member 40 of male garment 40 and toroidal gripper 54 of sheath member 46 in cavity 52.

Although the present invention has been described in some detail by way of illustration and example for purposes of clarity and understanding, it will, of course be understood that various changes and modifications may be made with the form, details, and arrangements of the parts without departing from the scope of the invention as set forth in the following claims.

What is claimed is:

1. An anti-herpes modality system adapted to be worn by a male partner and a female partner to prevent contact during sexual intercourse comprising, in combination:

a doubly sealed garment impermeable to the passage of herpes virus adapted to be worn by the female partner covering the herpes contagious genital area, said garment including a front wall portion having a generally circular hole therein at the genital area, said hole having a rim portion forming a biasable toroidal lock member, a cooperatively associated sheath member to be worn by the male partner, and having a generally cylindrical, elongated, flexible sheath wall impervious to the passage of herpes virus and adapted to fit around the penis of the male partner, said sheath wall having a closed end and an opposed end having an edge portion having a toroidal biasable gripper member, said sheath member passing through said hole formed by the rim portion of said garment, said biasable toroidal lock member secured to said rim portion and said toroidal lock member forming an external circular cavity, said biasable toroidal gripper of said sheath secured to said edge portion and being capable of stretching from an unbiased condition to fit over and form a double seal with said toroidal lock member and be removably positioned in said circular cavity, wherein said toroidal gripper is in a biased condition directly radially pressing upon said front wall portion of said garment and indirectly radially pressing said sheath wall against said penis, said toroidal lock member and said toroidal gripper being adapted to mutually removably engage one another to removably connect said sheath member with said front wall portion of said garment and to provide together by means of said toroidal lock member and said toroidal gripper said double seal to said garment against the passage of herpes virus.

2. A system according to claim 1, wherein said garment is configured as a pair of short pants, said garment being made of a soft, flexible material.

3. A system according to claim 1, wherein said biasable toroidal gripper is made of rubber.

4. A system according to claim 3, wherein said toroidal lock is made of rubber.

5. A system according to claim 1, wherein said toroidal lock is made of a biasable plastic.

* * * * *